(12) United States Patent
Petit et al.

(10) Patent No.: US 9,937,212 B2
(45) Date of Patent: *Apr. 10, 2018

(54) L. JOHNSONII LA1, B. LONGUM NCC2705 AND IMMUNE DISORDERS

(75) Inventors: Valerie Petit, Thonon-les-Bains (FR); Clara Lucia Garcia-Rodenas, Forel (CH); Monique Julita, Prilly (CH)

(73) Assignee: Nestec S.A., Vevey (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/805,228

(22) PCT Filed: Jun. 17, 2011

(86) PCT No.: PCT/EP2011/060099
§ 371 (c)(1),
(2), (4) Date: Dec. 18, 2012

(87) PCT Pub. No.: WO2011/157816
PCT Pub. Date: Dec. 22, 2011

(65) Prior Publication Data
US 2013/0089524 A1   Apr. 11, 2013

(30) Foreign Application Priority Data
Jun. 18, 2010   (EP) .................................... 10166526

(51) Int. Cl.
| | | |
|---|---|---|
| A61K 35/742 | (2015.01) | |
| A61K 35/745 | (2015.01) | |
| A61K 35/747 | (2015.01) | |
| A23L 33/135 | (2016.01) | |

(52) U.S. Cl.
CPC .......... *A61K 35/742* (2013.01); *A23L 33/135* (2016.08); *A61K 35/745* (2013.01); *A61K 35/747* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 5,578,302 A | 11/1996 | Brassart et al. | |
| 6,399,124 B1 * | 6/2002 | Lesens et al. | 426/61 |
| 6,929,793 B2 * | 8/2005 | Spivey-Krobath et al. | 424/93.4 |
| 7,183,101 B2 * | 2/2007 | Arigoni et al. | 435/252.9 |
| 2004/0126870 A1 * | 7/2004 | Arigoni | A23C 9/1234 435/252.2 |
| 2011/0002900 A1 * | 1/2011 | Mingrone et al. | 424/93.44 |

FOREIGN PATENT DOCUMENTS

| | | |
|---|---|---|
| EP | 1227152 | 7/2002 |
| EP | 2133088 | 12/2009 |
| WO | 02/28402 | 4/2002 |
| WO | 2007/020884 | 2/2007 |
| WO | 2010000580 | 1/2010 |
| WO | WO 2010/130663 * | 5/2010 ............. A61K 35/74 |
| WO | WO2010/130710 * | 11/2010 |

OTHER PUBLICATIONS

Parche et al., Journal of Bacteriology, Feb. 2006, vol. 188, No. 4, pp. 1260-1265.*
Nestle et al., Nestle Research Center, 2003, Developing foods with proven health benefits, slides 1-13, pp. 1-7; retrieved from the Internet:http://www.foodnet.cz/soubor.php?id=2382 &kontrola=17e60bcf86cce38a51992b7de0c58d3c &foodnet=451e70a5.*
Collado et al., Development of New Probiotics by Strain Combinations: Is it Possible to Improve the Adhesion to Intestinal Mucus?, Journal of Dairy Science, vol. 90 No. 6, 2007, pp. 2710-2716.*
Timmerman et al., Monostrain, multistrain and multispecies probiotics—A comparison of functionality and efficacy, International Journal of Food Microbiology 96 (2004), pp. 219-233.*
Cruchet et al., Effect of the Ingestion of a Dietary Product Containing Lactobacillus johnsonii La1 on Helicobacter pylori Colonization in Children, Nutrition 19:716-721, 2003.*
Bajaj-Elliott et al., Modulation of host antimicrobial peptide (beta-defensins 1 and 2) expression dudring gastritis, Gut 2002; 51:356-361.*
Doss et al., "Human defensins and LL-37 in mucosal immunity", Journal of Leukocyte Biology, vol. 87, Jan. 2010, pp. 79-92, XP009141276.
Gianotti et al., "A randomized double-blind trial on perioperative administration of probiotics in colorectal cancer patients", World Journal of Gastroenterology, vol. 16, No. 2, Jan. 14, 2010, pp. 167-175, XP009141271.
Rivas-Santiago et al., "Susceptibility to Infectious Diseases Based on Antimicrobial Peptide Production", Infection and Immunity, vol. 77, No. 11, Nov. 2009, pp. 4690-4695, XP009141272.
Denou et al., "A Mesocosm of Lactobacillus johnsonii, Bifidobacterium longum, and *Escherichia coli* in the Mouse Gut", DNA and Cell Biology, 2009, pp. 413-422, vol. 28, No. 8.
International Search Report & Written Opinion dated Aug. 12, 2011 for corresponding Intl. Appln. No. PCT/EP2011/060099.
Japan Office Action for Application No. P2013-514730, Dispatch No. 544374, dated Dec. 1, 2015, 8 pages.

* cited by examiner

*Primary Examiner* — Thane Underdahl
*Assistant Examiner* — Evelyn Y Pyla
(74) *Attorney, Agent, or Firm* — K&L Gates LLP

(57) ABSTRACT

The present invention generally relates to the field of probiotics, and in particular to preventing and/or treating inflammatory and infectious disorders, for example by boosting the endogenous antimicrobial defences. One embodiment of the present invention is a composition comprising a combination of *L. johnsonii* (La1, NCC 533, deposit number CNCM I-1225) and *Bifidobacterium longum* NCC2705 (deposit number CNCM I-2618). This composition may be used in the treatment or prevention of disorders related to the immune system including infections.

13 Claims, 1 Drawing Sheet

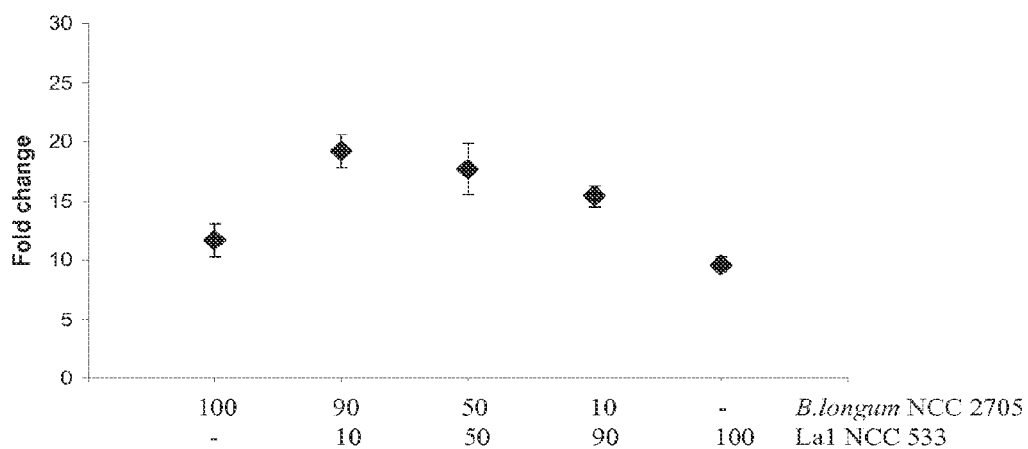
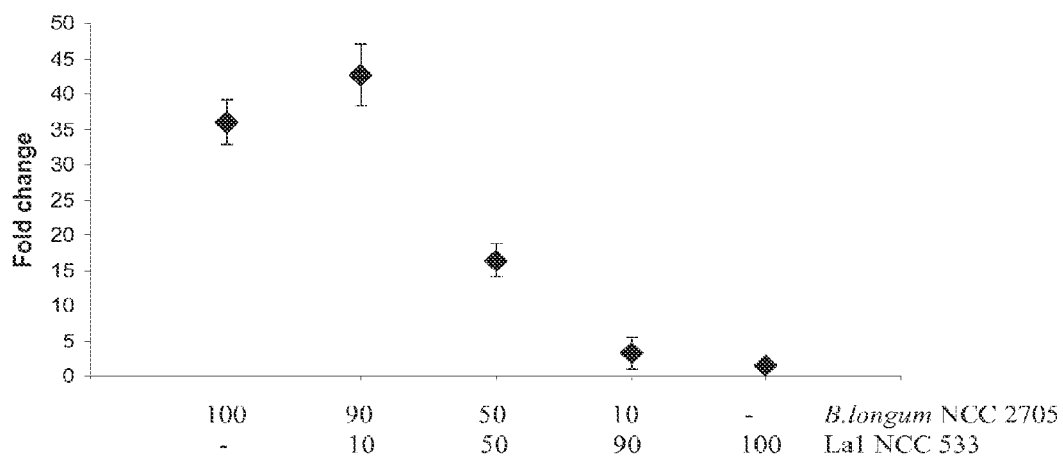

L. JOHNSONII LA1, B. LONGUM NCC2705 AND IMMUNE DISORDERS

CROSS REFERENCE TO RELATED APPLICATIONS

The present application is a National Stage of International Application No. PCT/EP2011/060099, filed on Jun. 17, 2011, which claims priority to European Patent Application No. 10166526.3, filed on Jun. 18, 2010, the entire contents of which are being incorporated herein by reference.

FIELD OF THE INVENTION

The present invention generally relates to the field of probiotics, and in particular to preventing and/or treating inflammatory and infectious disorders, for example by boosting the endogenous antimicrobial defences. One embodiment of the present invention is a composition comprising a combination of *Lactobacillus johnsonii* (La1, NCC533 deposit number CNCM I-1225) and *Bifidobacterium longum* (NCC2705 deposit number CNCM I-2618). This composition may be used in the treatment or prevention of disorders related to the immune system including infections.

BACKGROUND OF THE INVENTION

Our environment is contaminated by a vast array of potentially pathogenic microorganisms. Skin keratinocytes, epithelial cells lining the gastrointestinal tract, respiratory tract, genito-urinary tract all provide a physical barrier that protect against microbial intrusion into the body.

In addition, these epithelia contribute to the host defences by producing and secreting antimicrobials to limit access of bacteria and other microorganisms. These antimicrobial molecules constitute key components of the basic defence line of the innate immunity.

Defensins are one of the most important classes of antimicrobial peptides in humans. Defensins are produced by epithelial cells of the lung, skin, oral cavity, genitourinary, respiratory and gastrointestinal tract. Among these, there is the family of β-defensins including the defensin 1 (hBD1) and 2 (hBD2).

HBD1 is expressed in various mucosal surfaces such as oral mucosa, salivary gland, stomach, small intestine, colon, liver and pancreas. HBD2 is also present in epithelial cells at multiple mucosal surfaces including that of gastrointestinal tract. Moreover, these two defensins are also present in saliva and airway surface fluid (Cunliffe, R. N. and Mahida, Y. R. 2004, J Leukoc. Biol. 75:49-58).

HBD2 is present at very low levels in normal tissues, and its expression is up-regulated by bacteria and pro-inflammatory cytokines. Contrary to hBD2, HBD1 is constitutively expressed. HBD1 has never been shown to be consistently up-regulated by bacteria or inflammation (Ou, G., et al., 2009, Scand. J Immunol 69:150-161).

Probiotics are well known to be able to reinforce the various lines of gut defence: immune exclusion, immune elimination, and immune regulation. Probiotics are also known stimulate non-specific host resistance to microbial pathogens and thereby aid in their eradication.

However, despite this, the expression of the constitutive hBD1 has been reported as unaffected by probiotic bacteria (O'Neil, D. A. et al., J Immunol 163:6718-6724) and as very mildly upregulated by commensal (*Escherichia coli*) and pathogenic (*Salmonella typhimurium*) strains (Ou, G., et al., 2009, Scand. J Immunol 69:150-161).

SUMMARY

It would be desirable to have available an effective natural composition with no undesired side effects, that can be used to up-regulate the expression of β-defensins, in particular of defensin 1 (hBD1) and 2 (hBD2) in order to boost the endogenous antimicrobial defenses to be useful in the treatment or prevention of disorders related to the immune system including infections.

Ideally the natural composition should contain probiotic cultures that are well accepted today and recognized by consumers for delivering heath benefits.

Probiotics being able to stimulate the expression of β-defensins effectively, in particular of defensin 1 (hBD1) and 2 (hBD2), would have an additional and/or an improved health benefit, which would allow the probiotics to be particular effective, e.g., in the treatment or prevention of disorders related to the immune system.

The present inventors have addressed this need.

Hence, it was the object of the present invention to improve the state of the art and to provide a natural and effective composition, that allows preventing and/or treating inflammatory and infectious disorders, in particular by boosting the endogenous antimicrobial defences and that fulfils the requirements listed above.

The inventors were surprised to see that they could achieve the object of the present invention by the subject matter of the independent claims. The dependant claims further define preferred embodiments of the present invention.

The subject matter of the present invention strengthens the mammalian endogenous antimicrobial defences by administering a product containing micro-organisms, such as non-replicating micro-organism, for example heat-treated microorganisms.

The inventors describe that a combination of *L. johnsonii* (La1, NCC 533, deposit number CNCM I-1225) and *Bifidobacterium longum* NCC2705 (deposit number CNCM I-2618) has a superior effect on the induction of antimicrobial peptide expression.

It was found, for example, that a combination of *L. johnsonii* (La1, NCC 533, deposit number CNCM I-1225) and *Bifidobacterium longum* NCC2705 (deposit number CNCM I-2618) triggers an up-regulation of both, hBD1 and hBD2 mRNA expression, effectively. Remarkably, the observed effect was significantly more pronounced than it could have been expected based on the results produced by the two bacterial strains tested individually.

It was observed that different combinations of the two probiotics caused an up-regulation of hBD1 mRNA expression that was higher than the effect induced by both strains tested individually.

Concerning hBD2 expression, it could be shown that that, for example, the combination of the two probiotics with a high dose of *B. longum* (NCC2705, deposit number CNCM I-2618) (90) and low dose of *L. johnsonii* (La1, NCC 533, deposit number CNCM I-1225) (10) resulted in an increased induction of hBD2 compared to that obtained with the individual strains alone.

Hence, the inventors have found that a combination of *L. johnsonii* (La1, NCC 533, deposit number CNCM I-1225) and *Bifidobacterium longum* NCC2705 (deposit number CNCM I-2618) act synergistically in inducing the expression of antimicrobial peptides, e.g., of hBD1 and/or hBD2.

HBD1 and hBD2 display antibacterial activity against a broad spectrum of bacteria including *E. coli* and *Pseudomonas aeruginosa, H. pylori* (Nuding, S., et al., 2009, Microbes. Infect. 11:384-393) and also against yeasts such as *Candida albicans* (O'Neil, D. A. 2003, Mol. Immunol 40:445-450) and viruses (human immunodeficiency virus) (Kota, S. Et al., 2008, J. Biol. Chem 283:22417-22429). Thus, these antimicrobial peptides may reinforce the mucosal barrier and consequently limit bacterial adherence and invasion.

More and more evidence indicate that the levels of defensins are reduced in certain pathophysiological conditions and that this is a risk factor in the pathogenesis and complications of infectious and inflammatory diseases such as (Doss, M. et al., 2010, J Leukoc. Biol. 87:79-92; Rivas-Santiago, B. et al., 2009, Infect. Immun. 77:4690-4695):

In the Respiratory Tract:
cystic fibrosis, reactive airways disease, lung infections and tobacco smoking, asthma, pneumonia, rhinitis, otitis, sinusitis, tuberculosis In the Gastrointestinal Tract:
Crohn's disease (colon and ileum), ulcerative colitis, celiac disease, intestinal immaturity, gastritis and gastric ulcer induced by *Helicobacter pylori* infection, infectious diarrhea, necrotising enterocolitis, antibiotic-associated diarrhea.

In the Genitourinary Tract:
Bacterial vaginosis, HIV, urinary infection

In the Skin:
Atopic dermatitis, chronic ulcer, carcinoma, atopic eczema, burn injury In the Oral Cavity:
HIV patients, tonsillitis, gingivitis, dental caries Keratitis in Eyes The results presented herein indicate that a combination of *L. johnsonii* (La1, NCC 533, deposit number CNCM I-1225) and *Bifidobacterium longum* NCC2705 (deposit number CNCM I-2618) has a surprisingly strong capacity to boost the endogenous antimicrobial defence based on synergistic action, and thus is more efficient in the prevention and treatment of SIBO (Small Intestinal Bacterial Overgrowth), inflammatory and infectious disorders.

One embodiment of the present invention relates hence to a composition comprising a combination of *L. johnsonii* (La1, NCC 533, deposit number CNCM I-1225) and *B. longum* NCC2705 (deposit number CNCM I-2618).

Any ratio of *L. johnsonii* (La1, NCC 533, deposit number CNCM I-1225) and *B. longum* NCC2705 (deposit number CNCM I-2618) may be used. All combinations will be more effective than corresponding amounts of the individual strains used alone.

However, it was found that the combination of *L. johnsonii* (La1, NCC 533, deposit number CNCM I-1225) and *B. longum* NCC2705 (deposit number CNCM I-2618) is in particularly effective, e.g., in the treatment or prevention of disorders related to the immune system, for example by boosting the endogenous β-defensin expression, if certain specific ratios of *L. johnsonii* (La1, NCC 533, deposit number CNCM I-1225) and *B. longum* NCC2705 (deposit number CNCM I-2618) are used.

Hence, the composition of the present invention may comprise *L. johnsonii* (La1, NCC 533, deposit number CNCM I-1225) and *B. longum* NCC2705 (deposit number CNCM I-2618) in a ratio in the range of about 10:90 to 5:95, preferably of about 50:50 to 5:95, for example of about 20:80 to 5:95.

For example, the composition of the present invention may comprise *L. johnsonii* (La1, NCC 533, deposit number CNCM I-1225) and *B. longum* NCC2705 (deposit number CNCM I-2618) in a ratio in the range of about 10:90.

The ratios may be calculated based on the number of colony forming units (cfu).

The compositions of the present invention may comprise *L. johnsonii* (La1, NCC 533, deposit number CNCM I-1225) and *B. longum* NCC2705 (deposit number CNCM I-2618) in an amount sufficient to at least partially treat disorders linked to the immune system and/or their complications. An amount adequate to accomplish this is defined as "a therapeutically effective dose". Amounts effective for this purpose will depend on a number of factors known to those of skill in the art such as the severity of the disease and the weight and general health state of the consumer, and on the effect of the food matrix.

In prophylactic applications, compositions according to the invention are administered to a consumer susceptible to or otherwise at risk of disorders linked to the immune system in an amount that is sufficient to at least partially reduce the risk of developing such disorders. Such an amount is defined to be "a prophylactic effective dose". Again, the precise amounts depend on a number of patient specific factors such as the patient's state of health and weight, and on the effect of the food matrix.

Those skilled in the art will be able to adjust the therapeutically effective dose and/or the prophylactic effective dose appropriately.

In general the composition of the present invention contains La1 in a therapeutically effective dose and/or in a prophylactic effective dose.

Typically, the therapeutically effective dose and/or the prophylactic effective dose is in the range of about 0.005 mg-1000 mg *L. johnsonii* (La1, NCC 533, deposit number CNCM I-1225) and *B. longum* NCC2705 (deposit number CNCM I-2618) per daily dose.

In terms of numerical amounts, *L. johnsonii* (La1, NCC 533, deposit number CNCM I-1225) and *B. longum* NCC2705 (deposit number CNCM I-2618) may be present in the composition in a combined amount corresponding to between $10^4$ and $10^{12}$ equivalent cfu/g of the dry composition. For example, the composition in accordance with the present invention may contain an amount of *L. johnsonii* (La1, NCC 533, deposit number CNCM I-1225) and *B. longum* NCC2705 (deposit number CNCM I-2618) corresponding to about $10^4$ to $10^{12}$ cfu per daily dose.

The composition of the present invention may contain about 0.005 mg-1000 mg *L. johnsonii* (La1, NCC 533, deposit number CNCM I-1225) and *B. longum* NCC2705 (deposit number CNCM I-2618) per daily dose.

The composition of the present invention may be any kind of composition. The composition may be to be administered orally, by inhalation, enterally, parenterally (subcutaneously or intramuscularly), topically or ocularly, intrarectally, intravaginally for example.

Hence, the composition of the present invention may be selected from the group consisting of food compositions, food products including pet foods, drinks, formulas for complete nutrition, nutritional supplements, nutraceuticals, food additives, pharmaceutical compositions, cosmetical compositions, topical compositions and medicaments.

The composition of the present invention may be for use in the treatment or prevention of disorders linked to the immune system including infections.

According to the present invention the disorders linked to the immune system may be treated or prevented by increasing endogenous β-defensin expression, e.g. hBD1 and/or hBD2 expression.

The composition of the present invention may also be for use in the treatment or prevention of disorders linked to a decreased β-defensin expression, e.g. hBD1 and/or hBD2 expression, such as microbial infections, for example.

The present invention also concerns the use of a combination of *L. johnsonii* (La1, NCC 533, deposit number CNCM I-1225) and *B. longum* NCC2705 (deposit number CNCM I-2618) in the preparation of a composition for the treatment or prevention of disorders linked to the immune system.

The disorder linked to the immune system may be selected from the group consisting of infections, in particular bacterial, viral, fungal and/or parasite infections; inflammations; phagocyte deficiencies; epithelial barrier defect or immune system immaturity, SIBO and combinations thereof.

In one embodiment the composition of the present invention may be for use in the treatment or prevention of microbial infections, such as viral, fungal and/or parasite infections.

The disorder linked to the immune system may also be selected from the group of disorders linked to a reduced level of β-defensins, in particular hBD1 and/or hBD2. Such disorders may be selected from the group consisting of cystic fibrosis, reactive airways disease, lung infections from tobacco smoking, asthma, pneumonia, rhinitis, otitis, sinusitis, tuberculosis, Crohn's disease (colon and ileum), ulcerative colitis, celiac disease, intestinal immaturity, epithelial barrier defect or immune system immaturity, SIBO, gastritis and gastric ulcer induced by *Helicobacter pylori* infection, infectious diarrhea, necrotising enterocolitis, antibiotic-associated diarrhea, bacterial vaginosis, HIV, urinary infection, atopic dermatitis, chronic ulcer, carcinoma, atopic eczema, burn injury, tonsillitis, gingivitis, dental caries, keratitis in eyes, and combinations thereof.

The composition of the present invention may be used to boost the endogenous antimicrobial defences. This may be achieved, for example, by boosting the endogenous hBD1, and/or hBD2 expression.

Prebiotics may be added. Prebiotics may support the growth of probiotics. Moreover, prebiotics may also act synergistically with viable probiotic bacteria that are present in the composition.

Those skilled in the art will understand that they can freely combine all features of the present invention described herein, without departing from the scope of the invention as disclosed. In particular, features described for the compositions of the present invention may be applied to the uses of the present invention and vice versa.

Further advantages and features of the present invention are apparent from the following Examples and Figures.

BRIEF DESCRIPTION OF THE DRAWINGS

FIG. 1 shows the effect of the combination of *B. longum* (NCC2705 deposit number CNCM I-2618) with *L. johnsonii* (La1, NCC 533, deposit number CNCM I-1225) on hBD1 mRNA expression. T84 cells were incubated for 4 h with various mixes containing various concentrations of both strains. Gene expression of hBD1 was analyzed by real-time PCR. The data represent the means±sem normalized to basal expression of non stimulated cells.

FIG. 2 shows the effect of the combination of *B. longum* (NCC2705 deposit number CNCM I-2618) with *L. johnsonii* (La1, NCC 533, deposit number CNCM I-1225) on hBD2 mRNA expression. T84 cells were incubated for 4 h with various mixes containing various concentrations of live strains. Gene expression of hBD2 was analyzed by real-time PCR. The data represent the means±sem normalized to basal expression of non stimulated cells.

DETAILED DESCRIPTION

Examples:
Experimental Protocol:
T84 cells were used from passage 30-40 and cultured in Dulbecco's modified essential medium/F-12 (Sigma D 6421) containing 5% of foetal calf serum (FCS) (Amined BioConcept) and 2 mM glutamine. Cells were seeded at a concentration of $2 \times 10^6$ cell/well in 6-well culture plates and grown as monolayers at 37° C. in a 5% $CO_2$-95% air atmosphere. Cells grown to 1 week after confluence were incubated with serum and antibiotic-free medium for at least 12 H. This step was necessary to eliminate serum-induced defensin expression and prevent any influence of antibiotics on the probiotics and on the cell immune response. Cells were further incubated with probiotics for 4 H. At the end of the incubation time, cells were washed with PBS and harvested with TriPure™ isolation reagent according to the supplier's protocol. Human hBD1 and hBD2 gene expression in the so-treated cells was assessed by quantitative PCR.

Bacterial strains used in this experiment are *B. longum* (NCC 2705 deposit number CNCM I-2618) and *L. johnsonii* (La1, NCC 533 deposit number CNCM I-1225).

Results:
As *B. longum* (NCC 2705 deposit number CNCM I-2618) and *L. johnsonii* (La1, NCC 533 deposit number CNCM I-1225) up-regulate specifically the mRNA expression of hBD2 and hBD1 respectively, the inventors investigated the effects of a combined preparation of these two strains on intestinal antimicrobial defenses. We observed that the different combinations of the two probiotics caused an up-regulation of hBD1 mRNA expression that was higher than the effect induced by both strains tested individually (FIG. 1).

Concerning hBD2 expression, the data revealed that, for example, the combination of the two probiotics with a high dose of *B. longum* (NCC2705) (90) and low dose of La1 (NCC533) (10) resulted in an increased induction of hBD2 compared to that obtained with the individual strains alone (FIG. 2).

The invention claimed is:
1. A method for the treatment of an immune disorder related to the immune system, the method comprising: administering to an individual in need of same a composition that boosts the endogenous antimicrobial defenses by boosting the endogenous hBD1 expression, the composition comprising a probiotic mixture consisting of *L. johnsonii* (La1, NCC 533, deposit number CNCM I-1225) and *B. longum* NCC2705 (deposit number CNCM I-2618) in a ratio of 10:90 to 5:95, the *L. johnsonii* La1 and the *B. longum* NCC2705 are heat-treated non-replicating microorganisms.

2. The method of claim 1, wherein the immune disorder related to the immune system is selected from the group consisting of diarrhea, fungal infections, ulcerative colitis, phagocyte deficiencies, epithelial barrier defect, immune system immaturity, small intestinal bacterial overgrowth (SIBO) and combinations thereof.

3. The method of claim 1, wherein the disorder related to the immune system is selected from the group of disorders linked to a reduced level of defensins, in particular hBD1 and hBD2.

4. The method of claim 3, wherein the disorder linked to a reduced level of defensins is selected from the group consisting of cystic fibrosis, reactive airways disease, lung infections and tobacco smoking, asthma, pneumonia, rhinitis, otitis, sinusitis, tuberculosis, Crohn's disease (colon and ileum), ulcerative colitis, celiac disease, intestinal immaturity, gastritis and gastric ulcer induced by *Helicobacter pylori* infection, infectious diarrhea, necrotising enterocolitis, antibiotic-associated diarrhea, bacterial vaginosis, HIV, urinary infection, atopic dermatitis, chronic ulcer, carcinoma, atopic eczema, burn injury, tonsillitis, gingivitis, dental caries, keratitis in eyes.

5. The method of claim 1, further comprising boosting hBD1 and hBD2 expression.

6. The method of claim 1, further comprising boosting the endogenous hBD2 expression.

7. The method of claim 1, wherein the ratio of the *L. johnsonii* La1 to the *B. longum* NCC2705 is about 10:90.

8. The method of claim 1, wherein the *L. johnsonii* La1 and the *B. longum* NCC2705 are present in the composition in a combined amount corresponding to between $10^4$ and $10^{12}$ cfu/g of the composition.

9. The method of claim 1, wherein the composition is administered to the individual to provide a combined amount of the *L. johnsonii* La1 and the *B. longum* NCC2705 corresponding to between $10^4$ and $10^{12}$ cfu/day.

10. A method for the treatment of an immune disorder selected from the group consisting of diarrhea, fungal infections, ulcerative colitis, phagocyte deficiencies, epithelial barrier defect, immune system immaturity, small intestinal bacterial overgrowth (SIBO) and combinations thereof, the method comprising:

administering to an individual having the immune disorder a composition that boosts the endogenous antimicrobial defenses by boosting the endogenous hBD1 expression, the composition comprising a probiotic mixture consisting of *L. johnsonii* (La1, NCC 533, deposit number CNCM I-1225) and *B. longum* NCC2705 (deposit number CNCM I-2618) in a ratio of 10:90 to 5:95, the *L. johnsonii* La1 and the *B. longum* NCC2705 are heat-treated non-replicating microorganisms.

11. The method of claim 10, wherein the ratio of the *L. johnsonii* La1 to the *B. longum* NCC2705 is about 10:90.

12. The method of claim 10, wherein the *L. johnsonii* La1 and the *B. longum* NCC2705 are present in the composition in a combined amount corresponding to between $10^4$ and $10^{12}$ cfu/g of the composition.

13. The method of claim 10, wherein the composition is administered to the individual to provide a combined amount of the *L. johnsonii* La1 and the *B. longum* NCC2705 corresponding to between $10^4$ and $10^{12}$ cfu/day.

* * * * *